United States Patent
Liu et al.

(10) Patent No.: US 10,138,275 B2
(45) Date of Patent: *Nov. 27, 2018

(54) CRYSTALLINE POWDER OF CYCLIC PEPTIDE COMPOUND, PREPARATION METHOD FOR SAME, AND USES THEREOF

(71) Applicant: SHANGHAI TECHWELL BIOPHARMACEUTICAL CO., LTD, Shanghai (CN)

(72) Inventors: Shidong Liu, Shanghai (CN); Xiusheng Wang, Shanghai (CN); Zhijun Tang, Shanghai (CN); Xiaoming Ji, Shanghai (CN)

(73) Assignee: SHANGHAI TECHWELL BIOPHARMACEUTICAL CO., LTD., Shanghai (CN)

( * ) Notice: Subject to any disclaimer, the term of this patent is extended or adjusted under 35 U.S.C. 154(b) by 46 days.

This patent is subject to a terminal disclaimer.

(21) Appl. No.: 15/314,799

(22) PCT Filed: May 29, 2015

(86) PCT No.: PCT/CN2015/080224
§ 371 (c)(1),
(2) Date: Nov. 29, 2016

(87) PCT Pub. No.: WO2015/180680
PCT Pub. Date: Dec. 3, 2015

(65) Prior Publication Data
US 2017/0101443 A1    Apr. 13, 2017

(30) Foreign Application Priority Data
May 29, 2014 (CN) .......................... 2014 1 0235522

(51) Int. Cl.
C07K 7/56 (2006.01)
A61K 38/12 (2006.01)
C07K 1/02 (2006.01)
A61K 38/00 (2006.01)

(52) U.S. Cl.
CPC ............... *C07K 7/56* (2013.01); *A61K 38/12* (2013.01); *C07K 1/02* (2013.01); *A61K 38/00* (2013.01)

(58) Field of Classification Search
None
See application file for complete search history.

(56) References Cited

FOREIGN PATENT DOCUMENTS

WO    03/018615 A1    3/2003

OTHER PUBLICATIONS

International Search Report, dated Aug. 20, 2015, International Patent Application No. PCT/CN2015/080224 with English translation (5 pages).

*Primary Examiner* — Christina Bradley
(74) *Attorney, Agent, or Firm* — Hamre, Schumann, Mueller & Larson, P.C.

(57) ABSTRACT

Disclosed is a crystalline powder of a cyclic peptide compound, represented by formula I is the structure of same, and, also disclosed are a preparation method for same and uses thereof.

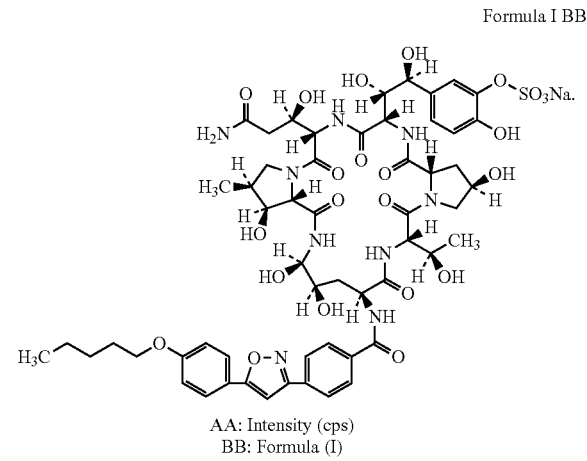

AA: Intensity (cps)
BB: Formula (I)

30 Claims, 1 Drawing Sheet

CRYSTALLINE POWDER OF CYCLIC PEPTIDE COMPOUND, PREPARATION METHOD FOR SAME, AND USES THEREOF

TECHNICAL FIELD

The present invention relates to crystalline powder of a compound, and particularly, to crystalline powder of a cyclic peptide compound as well as the preparation method and uses thereof.

BACKGROUND

Micafungin is a novel anti-fungal drug of pneumocandins, and it inhibits the synthesis of a fungi cell wall component, i.e. β-1,3-D-glucan synthase, whereby destroying the structure of fungal cells and thus leading to cytolysis. Micafungin is widely used for treating various infections, such as infections caused by *Aspergillus, Candida, Cryptococcus, Mucor, Actinomyces, Histoplasma, Dermatophytes* and *Fusarium* and the like.

Micafungin Sodium (also named as FK463) is the active pharmaceutical ingredient of the marketed drug, Mycamine. The chemical structure of micafungin Sodium is shown as follows:

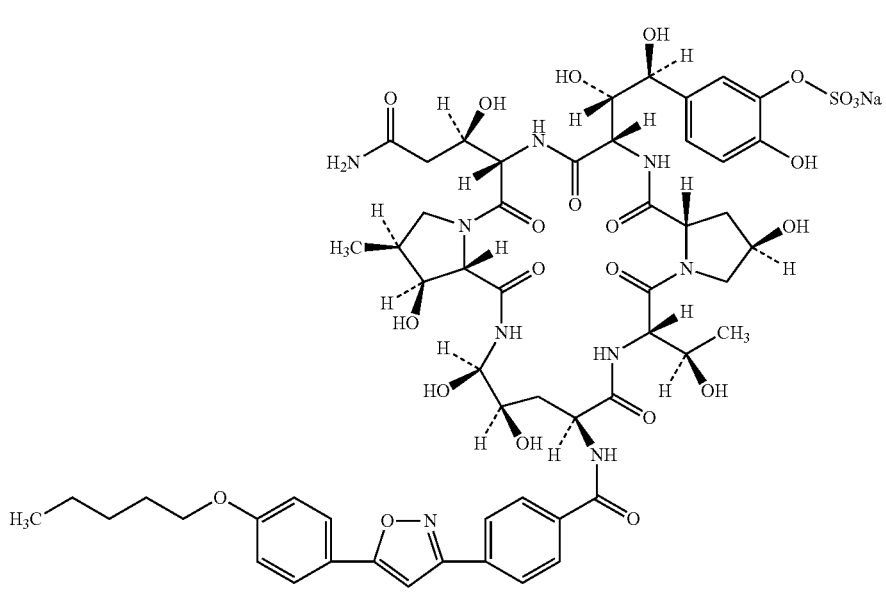

Formula I

Sodium

5-[(1S,2S)-2-[(3S,6S,9S,11R,15S,18S,20R,21R,24S,25S,26S)-3-[(R)-2-carbamoyl-1-hy droxyethyl]-11,20,21,25-tetrahydroxy-15-[(R)-1-hydroxyethyl]-26-methyl-2,5,8,14,17,23-hexaoxo-18-[4-[5-(4-pentoxyphenyl)isoxazol-3-yl]benzoylamino]-1,4,7,13,16,22-hex aazatricyclo[22.3.0.0.0$^{9,13}$]heptacosan-6-yl]-1,2-dihydroxyethyl]-2-hydroxy phenyl sulfate.

The compound of formula I is a polypeptide compound with poor stability, and its quality and efficacy are affected by degradation products generated during transportation or long-term storage. Furthermore, the compound of formula I is difficult to be crystallized and generally it is in an amorphous state.

U.S. Pat. Nos. 6,107,458 and 7,199,248 and WO 96/111210 disclosed methods for preparing and purifying the compounds of Formula I. Wherein, in U.S. Pat. No. 7,199,248, Micafungin DIPEA (diisopropylethylamine) salt was purified through filtration and chromatographic separation, and then precipitated with acetone and ethyl acetate to give the amorphous form of the compound of formula I.

Atsushi Ohigashi et al., "Process Development of Micafungin, a Novel Lipopeptide Antifungal Agent", *Journal of Synthesis Organic Chemistry*, 2006, Vol 64, (12), described that the compound of formula I can be precipitated by adding a mixture of acetone and ethyl acetate to the elution solution of the compound of formula I from ion exchange, so as to give the amorphous compound of formula I. Before drying, the content of solvent in the precipitate of the compound of formula I was high (Dry/Wet=0.25), and the precipitate of the compound of formula I contained about 75% of solvent. To reduce the content of solvent to below the standard value, the drying time has to be extended, which, however, will cause an increase in the degradation products of the compound of formula I and a reduction in quality.

In addition, the patent application WO 03/018615 of Fujisawa Pharmaceutical Co., Ltd. disclosed a new crystal form of the compound of the formula I and a preparation method thereof. In WO03/018615, the compound of formula I in amorphous form was dissolved in an aqueous alcohol solution or aqueous acetone solution, and a solvent, such as ethyl acetate, methylene chloride, acetone and acetonitrile was added, so as to give the B82-type acicular crystals of the compound of formula I. The crystal was obtained in an organic solvent, has a needle shape under microscope, and has peaks at the following 2θ angles in the X-ray powder diffraction pattern: 4.6°, 5.5°, 9.0°, 9.8°, 16.9°.

In "Study of Industrial Manufacturing Methods for Micafungin (FK463)", *Seihutsu kogaku Kaishi*, 2005, Vol 83, YAMASHITA et al., from Fujisawa Pharmaceutical Co., Ltd., mentioned that needle-like crystals of FK463 were successfully obtained through optimization of solvent and control of pH. However, no specific embodiments and crystal data were disclosed. Since the prior patent application WO03/018615 of the company disclosed the B82-type needle-like crystals of the compounds of formula I, it can be seen that what YAMASHITA et al. obtained was also the B82-type needle-like crystal.

The present inventors prepared the B82-type acicular crystal according to the method of Example 1 in WO03/018615, and the resultant crystal was observed with an optical microscope, which reveals that the crystal is about 1 μm in size and has a fine-needle shape; d50 of the obtained crystals was determined as 0.2-1.0 um by Malven particle size analyzer. When the crystals were subjected to subsequent processing steps, such as filtration, drying or the like, the present inventors found that, because the B82-type crystals essentially have a fine-needle morphology, it is difficult to filter the crystals of the compound of formula I and the operation needs a long time. Before drying of the crystals, the content of solvent in the compound of formula I (Dry/Wet) was about 0.25, and a large amount of organic solvent was trapped in the crystal. To render the content of solvent in compliance with the requirements for active pharmaceutical ingredients (API), the drying temperature or the drying time has to be increased during the drying process. Such drying process, however, will increase the degradation product of the compound of formula I, seriously affecting the quality and stability of API. Upon study on the dried crystalline powder obtained from the needle-like crystal of B82 type, the inventors found that the bulk density of the needle-like crystal of B82 type is about 0.8 g/mL, which is relatively dense and unfavorable to the volatilization of solvents during the drying process of the crystalline powder, and thus directly affects the drying process; furthermore, when exposed to the environment, the crystal of B82 type is inclined to absorb moisture and has poor stability.

Therefore, there is an urgent need in the art to obtain a stable form of the compounds of formula I with regular morphology and lower bulk density, which can be easily filtered and dried, thereby achieving better commercial production.

SUMMARY OF THE INVENTION

One object of the present invention is to provide a crystalline powder of the compound of formula I.

Another object of the present invention is to provide the preparation method for the crystalline powder.

Another object of the present invention is to provide uses of the crystalline powder.

Crystalline Powder of the Compound of Formula I

In the present invention, a crystalline powder of the compound of formula I is provided.

A crystalline powder of a cyclic peptide compound, the structure of which is shown in formula I, wherein the bulk density of the crystalline powder is less than 0.7 g/mL.

In another preferred embodiment of the present invention, the bulk density of the crystalline powder is less than 0.6 g/mL.

In another preferred embodiment of the present invention, the bulk density of the crystalline powder is less than 0.5 g/mL.

In another preferred embodiment of the present invention, d50 of the crystalline powder is 10-100 um.

In another preferred embodiment of the present invention, d50 of the crystalline powder is 20-50 um.

In another preferred embodiment of the present invention, d10 of the crystalline powder is 1-9 um.

In another preferred embodiment of the present invention, d10 of the crystalline powder is 1-5 um.

In another preferred embodiment of the present invention, before solid-liquid separation, d50 of the crystalline powder is 10-100 um.

In another preferred embodiment of the present invention, before solid-liquid separation, d50 of the crystalline powder is 20-50 um.

In another preferred embodiment of the present invention, before solid-liquid separation, d10 of the crystalline powder is 1-9 um.

In another preferred embodiment of the present invention, before solid-liquid separation, d10 of the crystalline powder is 3-6 um.

The B82-type needle-like crystals disclosed in WO03/018615 are in a morphology of fine needle. The crystals are difficult to be filtered or dried, and they also have poor stability. In order to obtain the compound of formula I with better stability and morphology, the inventors have screened solvent systems for crystallization by using different solvent combinations in a three-phase system. After a long period of research, the inventors have unexpectedly found that column-like crystals with regular morphology can be obtained in a specific three-phase solvent system. Afterwards, we have carried out a large number of solvent screening tests. A crystalline powder of the compound of formula I with better stability and better morphology was finally obtained, and a preparation method thereof was established. Compared with the needle-like crystal of B82 type disclosed in WO03/018615, the crystal of the present invention is a column-like crystal with big particle size and low bulk density which can be easily filtered, and the solvents can be easily removed therefrom.

Upon research, the inventors unexpectedly discovered that a column-like crystal of the compound of formula I with excellent morphology, i.e., a crystalline powder of the compound of formula I, can be obtained in an aqueous methanol/isobutanol, methanol/isopropanol, methanol/n-propanol solution, i.e., a three-phase system solution or four-phase solvent system, by technical means for reducing the solubility of the compound of formula I in a solution, such as reducing the temperature or adding an insoluble solvent. Before drying, the Dry/Wet (ratio of dry weight to wet weight) of the compound of formula I obtained by crystallization and filtration is high, the content of contained organic solvents is low, and after drying, the bulk density is low and the organic solvents can be easily removed.

Identification and Properties of the Crystalline Powder of the Compound of Formula I After obtaining the crystalline powder of the compound of formula I, properties thereof are further studied by several means and instruments.

"Bulk density of powder" is a measurement standard for the relative importance of the interaction between microparticles by comparing the bulk density and tapped density of the powder. Methods for measuring bulk density of powder are known in the art; for example, it can be determined by cylinder measurement, volumetric measurement, and container measurement. Bulk density of the crystalline powder of the compound of formula I according to the present invention is determined as less than 0.7 g/mL, preferably less than 0.6 g/mL, most preferably less than 0.5 g/mL, by cylinder measurement.

"Particle size distribution" can be determined by using Malvern particle size analyzer 2600C to analyze the size distribution (including d10 and d50) of the crystals before solid-liquid separation of the crystallizing liquid. Wherein, d10 and d50 are means known for indicating the particle size distribution. d50 refers to a value of particle size, and the size of 50 vol/% of particles is smaller than said value. D10 refers to a value of particle size, and the size of 10 vol/% of particles is smaller than said value. The preferred method for determining d10 and d50 is laser diffraction, d50 of the crystalline powder of the compound of formula I according to the present invention is determined as 10-100 um, and d10 is determined as 1-9 um. Preferably, d50 of the crystalline powder is 20-50 um, and d10 thereof is 1-5 um. Before solid-liquid separation, d50 of the crystalline powder of the compound of formula I is 10-100 um, and d10 thereof is 1-9 um. Preferably, d50 of the crystalline powder is 20-50 um, and d10 thereof is 3-6 um.

"Micro-analysis technology" serves the purpose of analyzing crystal forms through identification of the exterior shape of a crystal by using an optical microscope. Under an optical microscope, the crystalline powder of the compound of formula I according to the present invention is a column-like crystal. Preferably, before solid-liquid separation, the crystalline powder of the compound of formula I according to the present invention has a shape substantially identical with FIG. 1.

High performance liquid chromatography (HPLC) is a common method for determining the purity of a compound, wherein a liquid is used as the mobile phase and a high-pressure transfusion system is used for pumping the mobile phase, such as single solvents with different polarities, a mixture of solvents at different proportions, or buffers, into a column packed with a stationary phase. Each component is separated in the column, and then enters into a detector for detection, thereby analyzing a sample. In the present invention, HPLC is used for determining the purity of the compound of formula I and studying the stability of a sample. Conditions of the HPLC method are listed as follows:

Analysis Column: YMC-ODS 250×4.6 mm, 5 μm;
Mobile phase: acetonitrile:phosphate buffer (pH 3.0)=45:70;
Flow rate: 1 ml/min;
Column temperature: 35° C.;
Diluent: aqueous phosphate buffer;
Detection wavelength: 210 nm;
Injection volume: 10 μl.

Gas chromatography (GC) used to separate and measure trace impurities in a compound is an accurate, qualitative and quantitative method of analysis. In the present invention, the content of organic solvents in the crystalline powder of the compound of formula I obtained in the present invention is measured by gas chromatography (GC).

At present, X-ray powder diffraction, also called X-ray polycrystal diffraction (XRD or XRPD), is commonly used as the test method for determining the structure of crystal (i.e., crystal form). By using an X-ray powder diffractometer, a series of diffraction patterns are produced when X-ray passing through a crystal. In the pattern, different diffraction lines and the intensities thereof are determined by atomic clusters having certain structures, thereby determining the structure of a crystal. The methods for determining the X-ray powder diffraction pattern of a crystal are known in the art. For example, X-ray powder diffraction pattern can be obtained by using RIGAKU D/max 2550VB/PC X-ray powder diffractometer with a scanning rate of 2°/min and a copper radiation target.

The crystalline powder of the compound of formula I according to the present invention possesses a unique crystal morphology, and there are specific characteristic peaks in the X-ray powder diffraction pattern. Particularly, the crystalline powder of the compound of formula I according to the present invention possesses characteristic peaks at the following 2θ angles in the X-ray powder diffraction pattern: 4.4±0.2°, 5.2±0.2°, 8.5±0.2°, 9.6±0.2°; in a preferred embodiment, there are additional characteristic peaks at the following 2θ angles in the pattern: 7.5±0.2°, 8.8±0.2°, 16.6±0.2°, 13.7±0.2°, 22.5±0.2°; and in another preferred embodiment, there are additional characteristic peaks at the following 2θ angles in the pattern: 12.6±0.2°, 14.9±0.2°, 15.6±0.2°, 25.1±0.2°. In a preferred embodiment, the crystalline powder of the compound of formula I according to the present invention possesses characteristic peaks at the following 2θ angles in the X-ray powder diffraction pattern: 4.4±0.1°, 5.2±0.1°, 8.5±0.1°, 9.6±0.1°; in another preferred embodiment, there are additional characteristic peaks at the following 2θ angles in the pattern: 7.5±0.1°, 8.8±0.1°, 16.6±0.1°, 13.7±0.1°, 22.5±0.1°; and in another preferred embodiment, there are additional characteristic peaks at the following 2θ angles in the pattern: 12.6±0.1°, 14.9±0.1°, 15.6±0.1°, 25.1±0.1°. Preferably, the crystalline powder of the compound of formula I according to the present invention has an X-ray powder diffraction (XRPD) pattern substantially identical with FIG. 2.

Preparation of the Crystalline Powder of the Compound of Formula I

A preparation method for the crystalline powder of the compound of formula I is provided in the present invention, comprising the steps of:

(a) dissolving the compound of formula I in an aqueous mixed solution of alcohols;

(b) obtaining solids by reducing the temperature and/or adding an organic solvent (i);

(c) vacuum-drying the solids obtained in step (b) together with a water system, thereby obtaining the crystalline powder.

Wherein the mixed solution of alcohols in step (a) is selected from a group consisting of methanol/isobutanol, methanol/isopropanol, and methanol/n-propanol.

Wherein, in the aqueous mixed solution of alcohols in step (a), the volume ratio of the two alcohols is 0.01-100, preferably 0.05-20, and more preferably 0.1-10.

Wherein, in the aqueous mixed solution of alcohols in step (a), the ratio of total volume of the alcohol to the volume of water is 0.1 to 100, preferably 0.5 to 10, and more preferably 1 to 7.

Wherein, the temperature of dissolving in step (a) is 10-50° C., preferably, 20-40° C.

Wherein, in step (a), 1-500 mg/ml, preferably 5-100 mg/ml, more preferably 10-50 mg/ml of the compound of formula I is contained, based on the total volume of the solution.

Wherein, in step (b), the organic solvent (i) is selected from a group consisting of n-propanol, isopropanol, isobutanol, methyl acetate, ethyl acetate, n-propyl acetate, and isopropyl acetate.

Wherein, in step (b), the temperature is reduced to −40 to 35° C., preferably −20 to 35° C., more preferably −10 to 30° C., and most preferably −5 to 15° C.

Wherein the volume ratio of organic solvent (i) in step (b) to the aqueous mixed solution of alcohols in step (a) is 0.1 to 50, preferably 0.1 to 10, and more preferably 1-5.

Uses of the Crystalline Powder of the Compound of Formula I and the Composition Thereof The crystalline powder of the compound of formula I provided by the present invention also can be directly used in the preparation of medicaments for treating fungal infections. A pharmaceutical composition comprising the crystalline powder of the compound of formula I and a pharmaceutically acceptable carrier can also be provided.

Relevant Terms

As used herein, the term "crystal" means the solid of a molecule or atom complex showing specific arrangement.

As used herein, the term "solid-liquid separation" means a process wherein, after the compound of the formula I crystallizes and precipitates in a solvent, the solid and the liquid are separated by filtration.

As used herein, the term "Dry/Wet" and "ratio of dry weight to wet weight" can be used interchangeably, both of which refer to the ratio of the weight of a compound without solvent(s) to the weight of the compound with solvent(s). In the present invention, wet weight of crystals is obtained by filtering the crystallized solids until no noticeable droplet outflows and weighing the solids.

As used herein, "the compound of formula I", "compound I" and "the compound according to formula I" can be used interchangeably, all of which refers to a compound of the following structural formula:

The advantages of the invention mainly include:
1. Providing a crystalline powder of the compound of formula I with excellent morphology which can be easily filtered and dried.
2. Providing methods for preparing the crystalline powder of the compound of formula I, which methods are convenient for solid-liquid separation, easy for removal of residual solvent, and highly suitable for industrial production.

MODE FOR CARRYING OUT THE INVENTION

The invention will be further illustrated with reference to the following specific examples. It is to be understood that

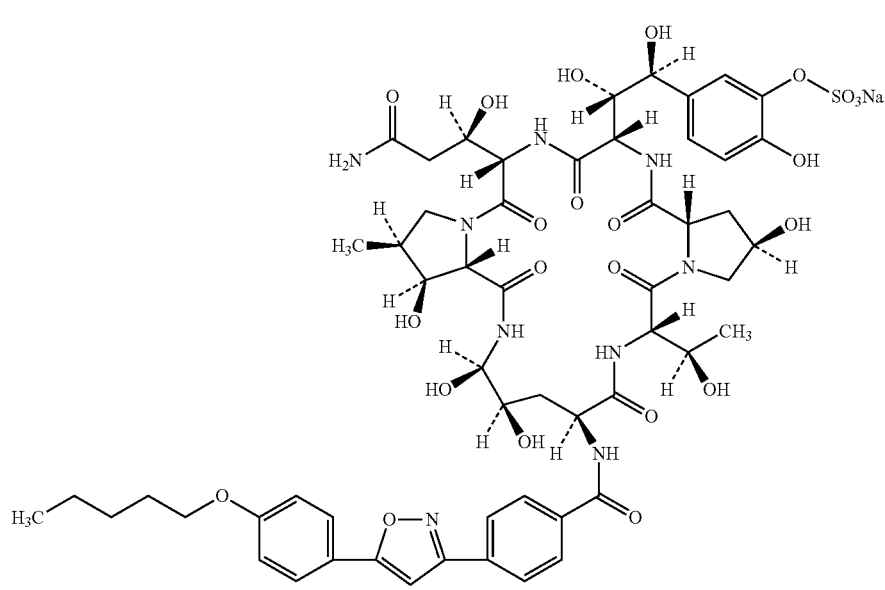

Formula I

The compound of formula I can be obtained by routine methods in the art, for example (but not limited to), the preparation method disclosed in WO96/11210; or alternatively, the compound can be commercially obtained, such as from Fujisawa, Japan.

As used herein, the term "pharmaceutically acceptable carrier" refers to the carriers that can be used in the administration of therapeutics, including various excipients and diluents. The term refers to the drug carriers which themselves are not necessary active ingredients, and will not produce undue toxicity upon administration. Suitable carriers are generally known to the skilled in the art. Detailed review regarding pharmaceutical acceptable excipients can be found in Remington's Pharmaceutical Sciences (Mack Pub. Co., N.J. 1991). Pharmaceutically acceptable excipients in a composition may include liquid, such as water, saline, glycol and ethanol. Additionally, auxiliary substances, such as disintegrating agents, wetting agents, emulsifying agents, pH buffering substances, etc., can be present in the carriers.

these examples are only intended to illustrate the invention, but not to limit the scope of the invention. In the following examples, the experimental methods without articulating specific experimental conditions are performed under routine conditions or as instructed by the manufacturer. Unless otherwise specified, all percentages, ratios, proportions or parts are by weight.

The unit of the weight/volume percentages in the invention is well known to the skilled in the art, for example, the weight of a solute in a 100 mL solution.

Unless otherwise defined, all scientific and technical terms used herein have the same meaning as commonly understood by the skilled in the art. Furthermore, any process or material similar or equivalent to those described herein can be used in the process of the present invention. The preferred embodiments and materials described herein are merely provided for illustration.

Example 1

Preparation of the Compound of Formula I

The solid amorphous powder of the compound of formula I was prepared according to the method of U.S. Pat. No. 7,199,248.

Comparative Example 1

Preparation of the Crystal of B82 Type

Needle-like crystals, i.e., crystals of B82 type, were obtained according to the method of Example 1 of WO03/018615. Particle size distribution was determined as d10=0.3 um, and d50=0.96 um. After filtration, wet crystals were weighed, and the ratio of dry weight to wet weight was calculated as 0.25. After drying, the bulk density was 0.85 g/mL, and the particle size was d10=0.25 um, d50=0.7 um.

Example 2

Preparation of the Crystalline Powder of the Compound of Formula I

Figure 1:
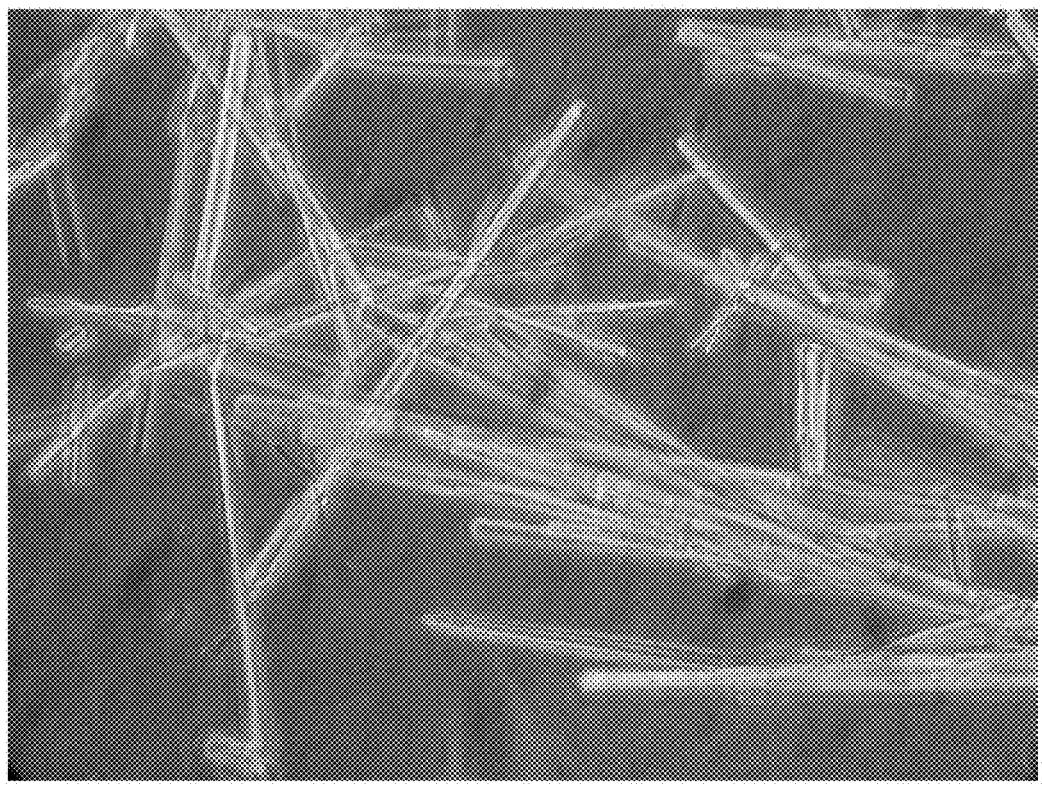
FIG. 1 shows a photograph of the crystal of the compound of formula I observed under a microscope before solid-liquid separation.
Figure 2:
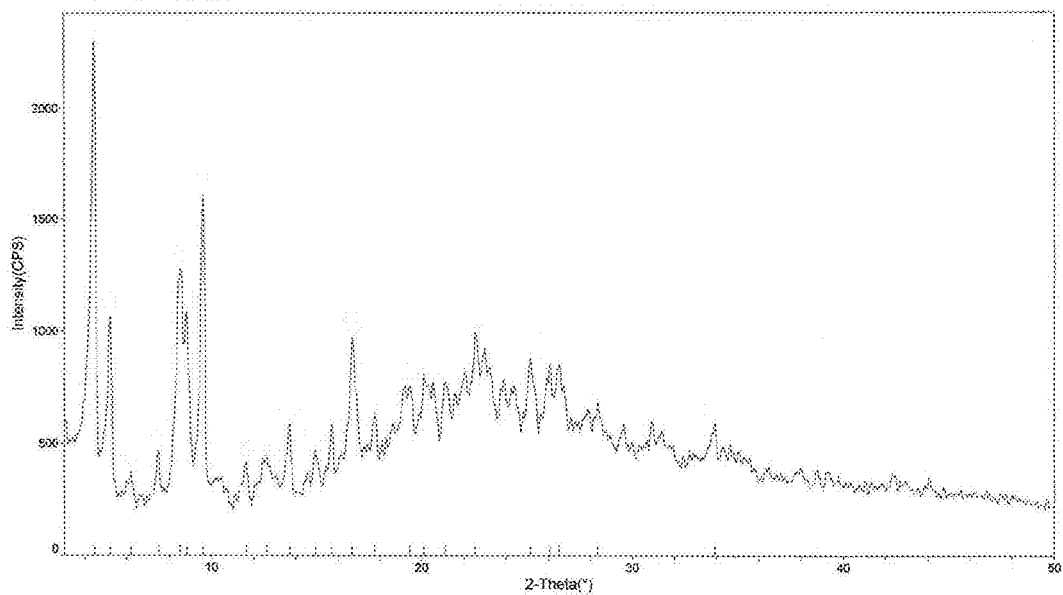
FIG. 2 shows the X-ray powder diffraction (XRPD) pattern of the crystalline powder of the compound of formula I.

At 25° C., 1 g of compound of formula I in amorphous form prepared in Example 1 was dissolved into 50 ml of aqueous methanol/isobutanol solution (isobutanol:water:methanol=8:2:1). The resultant solution was slowly cooled to 8° C., solids precipitated from the solution, and the system was stirred for 3.5 hours at this temperature, a large amount of solids precipitated. 90 ml of ethyl acetate were slowly added, and the solids were obtained by filtration. The solids were sampled before filtration and observed under a microscope (15×40), photograph of which can be found in FIG. 1, and the particle size distribution was determined as d10=3.3 um, and d50=32.6 um. After filtration, wet crystals were weighed, and the ratio of dry weight to wet weight was calculated as 0.45. The filtered solids were placed into a vacuum-drying oven, and a plate of tap water was put on the bottom of the vacuum-dryer. Crystalline powder was obtained by vacuum-drying. The bulk density of the crystalline powder was 0.45 g/mL, and the particle size thereof was d10=3 um, d50=31.9 um. The XRPD of the crystalline powder can be found in FIG. 2.

Example 3

Preparation of the Crystalline Powder of the Compound of Formula I

At 30° C., 2.5 g of crystals of B82 type prepared in Comparative Example 1 were dissolved into 50 ml of aqueous methanol/isobutanol solution (isobutanol:water:methanol=1:1:1), 50 ml of methyl acetate were slowly added, and solids were obtained by filtration. The solids were sampled before filtration and the particle size distribution was determined as d10=4.2 um, and d50=43.9 um. After filtration, wet crystals were weighed, and the ratio of dry weight to wet weight was calculated as 0.52. The filtered solids were placed into a vacuum-drying oven, and a plate of pure water was put on the bottom of the vacuum-dryer. Crystalline powder was obtained by vacuum-drying. The bulk density of the crystalline powder was 0.43 g/mL, and the particle size thereof was d10=3.7 um, d50=43.1 um.

Example 4

Preparation of the Crystalline Powder of the Compound of Formula I

At 10° C., 3 g of the compound of formula I in amorphous form prepared in Example 1 were dissolved into 600 ml of aqueous methanol/isobutanol solution (isobutanol:water:methanol=5:1:2), the obtained solution was cooled to −20° C., solids precipitated from the solution, the system was stirred for 12 hours, a large amount of solids precipitated, and the solids were obtained by filtration. The solids were sampled before filtration and the particle size distribution was determined as d10=5.7 um, and d50=54.3 um. After filtration, wet solids were weighed, and the ratio of dry weight to wet weight was calculated as 0.61. The filtered solids were placed into a vacuum-drying oven, and a plate of ice-water mixture was put on the bottom of the vacuum-dryer. Crystalline powder was obtained by vacuum-drying. The bulk density of the crystalline powder was 0.55 g/mL, and the particle size thereof was d10=5.1 um, d50=50 um.

Example 5

Preparation of the Crystalline Powder of the Compound of Formula I

At 50° C., 3 g of the compound of formula I in amorphous form prepared in Example 1 were dissolved into 120 ml of aqueous methanol/isopropanol solution (isopropanol:water:methanol=1:4:1), the obtained solution was cooled to 30° C., solids precipitated from the solution, the system was stirred for 30 mins, a large amount of solids precipitated, 200 ml of isopropanol were slowly added, and the solids were obtained by filtration. The solids were sampled before filtration and the particle size distribution was determined as d10=9 um, and d50=98.3 um. After filtration, wet solids were weighed, and the ratio of dry weight to wet weight was calculated as 0.66. The filtered solids were placed into a vacuum-drying oven, and a plate of tap water was put on the bottom of the vacuum-dryer. Crystalline powder was obtained by vacuum-drying. The bulk density of the crystalline powder was 0.6 g/mL, and the particle size thereof was d10=9 um, d50=97.7 um.

Example 6

Preparation of the Crystalline Powder of the Compound of Formula I

At 20° C., 1 g of the compound of formula I in amorphous form prepared in Example 1 was dissolved into 20 ml of aqueous methanol/isopropanol solution (isopropanol:water:methanol=10:2:1), 200 ml of n-propyl acetate were slowly added, and the solids were obtained by filtration. The solids were sampled before filtration and the particle size distribution was determined as d10=5.8 um, and d50=50 um. After filtration, wet solids were weighed, and the ratio of dry weight to wet weight was calculated as 0.6. The filtered solids were placed into a vacuum-drying oven, and a plate of tap water was put on the bottom of the vacuum-dryer. Crystalline powder was obtained by vacuum-drying. The bulk density of the crystalline powder was 0.49 g/mL, and the particle size thereof was d10=5um, d50=48.7 um.

Example 7

Preparation of the Crystalline Powder of the Compound of Formula I

At 18° C., 1.0 g of the compound of formula I in amorphous form prepared in Example 1 was dissolved into 100 ml of aqueous methanol/isopropanol solution (isopropanol:water:methanol=1:2:20), the obtained solution was cooled to −5° C., solids precipitated from the solution, the system was stirred for 4 hours, a large amount of solids precipitated, and the solids were obtained by filtration. The solids were sampled before filtration and the particle size distribution was determined as d10=1 um, and d50=10 um. After filtration, wet solids were weighed, and the ratio of dry weight to wet weight was calculated as 0.69. The filtered solids were placed into a vacuum-drying oven, and a plate of ice-water mixture was put on the bottom of the vacuum-dryer. Crystalline powder was obtained by vacuum-drying. The bulk density of the crystalline powder was 0.6 g/mL, and the particle size thereof was d10=1 um, d50=10 um.

Example 8

Preparation of the Crystalline Powder of the Compound of Formula I

At 30° C., 2 g of the compound of formula I in amorphous form prepared in Example 1 were dissolved into 20 ml of aqueous methanol/n-propanol solution (n-propanol:water:methanol=1:15:10), the obtained solution was cooled to −15° C., solids precipitated from the solution, the system was stirred for 2 hours, a large amount of solids precipitated, 100 ml of isopropyl acetate were slowly added, and the solids were obtained by filtration. The solids were sampled before filtration and the particle size distribution was determined as d10=5um, and d50=20 um. After filtration, wet solids were weighed, and the ratio of dry weight to wet weight was calculated as 0.45. The filtered solids were placed into a vacuum-drying oven, and a plate of tap water was put on the bottom of the vacuum-dryer. Crystalline powder was obtained by vacuum-drying. The bulk density of the crystalline powder was 0.38 g/mL, and the particle size thereof was d10=2.6 um, d50=18.7 um.

Example 9

Preparation of the Crystalline Powder of the Compound of Formula I

At 25° C., 4 g of the compound of formula I in amorphous form prepared in Example 1 were dissolved into 300 ml of aqueous methanol/n-propanol solution (n-propanol:water:methanol=20:2:1), 30 ml of isobutanol were slowly added, and the solids were obtained by filtration. The solids were sampled before filtration and the particle size distribution was determined as d10=1.8 um, and d50=23.9 um. After filtration, wet solids were weighed, and the ratio of dry weight to wet weight was calculated as 0.62. The filtered solids were placed into a vacuum-drying oven, and a plate of pure water was put on the bottom of the vacuum-dryer. Crystalline powder was obtained by vacuum-drying. The bulk density of the crystalline powder was 0.54 g/mL, and the particle size thereof was d10=1.3 um, d50=20 um.

Example 10

Preparation of the Crystalline Powder of the Compound of Formula I

At 40° C., 2.7 g of the compound of formula I in amorphous form prepared in Example 1 were dissolved into 80 ml of aqueous methanol/n-propanol solution (n-propanol:water:methanol=10:3:1), the obtained solution was cooled to −10° C., solids precipitated from the solution, the system was stirred for 1 hour, a large amount of solids precipitated, and the solids were obtained by filtration. The solids were sampled before filtration and the particle size distribution was determined as d10=8.7 um, and d50=100 um. After filtration, wet solids were weighed, and the ratio of dry weight to wet weight was calculated as 0.63. The filtered solids were placed into a vacuum-drying oven, and a plate of tap water was put on the bottom of the vacuum-dryer. Crystalline powder was obtained by vacuum-drying. The bulk density of the crystalline powder was 0.56 g/mL, and the particle size thereof was d10=8.3 um, d50=100 um.

Comparative Example 2

At 25° C., 0.8 g of the compound of formula I in amorphous form prepared in Example 1 were dissolved into 5 ml of aqueous methanol solution (methanol:water=3:2), the obtained solution was cooled to 0° C., solids precipitated from the solution, the system was stirred for 3 hours at this temperature, and the solids in a form of amorphous powder were obtained by filtration. The ratio of dry weight to wet weight was calculated as 0.13.

Comparative Example 3

At 32° C., 2.1 g of the compound of formula I in amorphous form prepared in Example 1 were dissolved into 50 ml of aqueous ethanol solution (ethanol:water=5:1), the obtained solution was cooled to 10° C., solids precipitated from the solution, the system was stirred for 5 hours at this temperature, and the solids in a form of amorphous powder were obtained by filtration. The ratio of dry weight to wet weight was calculated as 0.1.

Comparative Example 4

At 20° C., 3 g of the compound of formula I in amorphous form prepared in Example 1 were dissolved into 55 ml of aqueous n-propanol solution (n-propanol:water=1:1), the obtained solution was cooled to 0° C., solids precipitated from the solution, the system was stirred for 5 hours at this temperature, and the solids in a form of amorphous powder were obtained by filtration. The ratio of dry weight to wet weight was calculated as 0.19.

Comparative Example 5

At 45° C., 2.5 g of the compound of formula I in amorphous form prepared in Example 1 were dissolved into 32 ml of aqueous isopropanol solution (isopropanol:water=2:3), the obtained solution was cooled to 15° C., solids precipitated from the solution, the system was stirred for 1 hour at this temperature, and the solids in a form of amorphous powder were obtained by filtration. The ratio of dry weight to wet weight was calculated as 0.18.

Comparative Example 6

At 32° C., 1.7 g of the compound of formula I in amorphous form prepared in Example 1 were dissolved into 90 ml of aqueous isobutanol solution (isobutanol:water=4:1), the obtained solution was cooled to 10° C., solids precipitated from the solution, the system was stirred for 2 hours at this temperature, 20 ml of ethyl acetate was slowly added, and the solids in a form of amorphous powder were obtained by filtration. The ratio of dry weight to wet weight was calculated as 0.21.

Comparative Example 7

At 28° C., 1 g of the compound of formula I in amorphous form prepared in Example 1 was dissolved into 50 ml of aqueous n-butanol solution (n-butanol:water=9:1), the obtained solution was cooled to 0° C., 50 ml of methyl acetate were slowly added, and the solids in a form of amorphous powder were obtained by filtration. The ratio of dry weight to wet weight was calculated as 0.2.

Comparative Example 8

At 17° C., 1.2 g of the compound of formula I in amorphous form prepared in Example 1 were dissolved into 45 ml of aqueous acetone (acetone:water=4:1), the obtained solution was cooled to −5° C., solids precipitated from the solution, the system was stirred for 3.5 hours at this temperature, and the solids in a form of amorphous powder were obtained by filtration. The ratio of dry weight to wet weight was calculated as 0.15.

Comparative Example 9

At 25° C., 5 g of the compound of formula I in amorphous form prepared in Example 1 were dissolved into 150 ml of aqueous acetonitrile solution (acetonitrile:water=3:1), the obtained solution was cooled to 8° C., solids precipitated from the solution, the system was stirred for 2 hours at this temperature, 200 ml of iso-propyl acetate were slowly added, and the solids in a form of amorphous powder were obtained by filtration. The ratio of dry weight to wet weight was calculated as 0.09.

Comparative Example 10

At 30° C., 1.7 g of the compound of formula I in amorphous form prepared in Example 1 were dissolved into 100 ml of aqueous methanol/ethanol solution (methanol:ethanol:water=8:2:1), the obtained solution was cooled to 11° C., solids precipitated from the solution, the system was stirred for 6 hours at this temperature, 100 ml of ethyl acetate were slowly added, and the solids in a form of amorphous powder were obtained by filtration. The ratio of dry weight to wet weight was calculated as 0.23.

Comparative Example 11

At 23° C., 1.7 g of the compound of formula I in amorphous form prepared in Example 1 were dissolved into 100 ml of aqueous propanol/butanol solution (propanol:butanol:water=6:5:3), the obtained solution was cooled to −5° C., solids precipitated from the solution, the system was stirred for 7 hours at this temperature, and the solids in a form of amorphous powder were obtained by filtration. The ratio of dry weight to wet weight was calculated as 0.11.

Comparative Example 12

At 45° C., 4 g of the compound of formula I in amorphous form prepared in Example 1 were dissolved into 28 ml of aqueous methanol/n-butanol solution (methanol:n-butanol:water=1:7:2), the obtained solution was cooled to 11° C., solids precipitated from the solution, the system was stirred for 6 hours at this temperature, and the solids in a form of amorphous powder were obtained by filtration. The ratio of dry weight to wet weight was calculated as 0.18.

Comparative Example 13

At 20° C., 1 g of the compound of formula I in amorphous form prepared in Example 1 was dissolved into 70 ml of aqueous ethanol/butanol solution (ethanol:butanol:water=2:2:5), 100 ml of ethyl acetate were slowly added, and the solids in a form of amorphous powder were obtained by filtration. The ratio of dry weight to wet weight was calculated as 0.2.

Comparative Example 14

At 50° C., 3 g of the compound of formula I in amorphous form prepared in Example 1 were dissolved into 20 ml of aqueous methanol/acetonitrile solution (methanol:acetonitrile:water=4:1:2), the obtained solution was cooled to 25° C., solids precipitated from the solution, the system was stirred for 2 hours at this temperature, 70 ml of ethyl acetate were slowly added, and the solids in a form of amorphous powder were obtained by filtration. The ratio of dry weight to wet weight was calculated as 0.19.

Comparative Example 15

At 30° C., 2 g of the compound of formula I in amorphous form prepared in Example 1 were dissolved into 10 ml of aqueous methanol/acetone solution (methanol:acetone:water=9:2:2), the obtained solution was cooled to 5° C., solids precipitated from the solution, the system was stirred for 4 hours at this temperature, 50 ml of ethyl acetate were slowly added, and the solids in a form of amorphous powder were obtained by filtration. The ratio of dry weight to wet weight was calculated as 0.15.

Example 11

In this example, the precipitated solids from Examples 2-10 and Comparative Examples 1-3 were filtered through a Buchner funnel until no noticeable droplet outflowed, and the filtration processes were compared. Specific results are shown in the following table:

| Sample | Particle size distribution | Time for filtration |
| --- | --- | --- |
| Example 2 | d10 = 3.3 um, d50 = 32.6 um | 10 min |
| Example 3 | d10 = 4.2 um, d50 = 43.9 um | 20 min |
| Example 4 | d10 = 5.7 um, d50 = 54.3 um | 17 min |
| Example 5 | d10 = 9 um, d50 = 98.3 um | 18 min |
| Example 6 | d10 = 5.8 um, d50 = 50 um | 9 min |
| Example 7 | d10 = 1 um, d50 = 10 um | 23 min |
| Example 8 | d10 = 3 um, d50 = 20 um | 20 min |
| Example 9 | d10 = 1.8 um, d50 = 23.9 um | 27 min |
| Example 10 | d10 = 8.7 um, d50 = 100 um | 16 min |
| Comparative Example 1 | d10 = 0.3 um, d50 = 0.96 um | 90 min |
| Comparative Example 2 | / | 150 min |
| Comparative Example 3 | / | 300 min |

In Examples 2-10, 1-4 g of the compound of formula I were used to prepare the crystalline powder of the compound of formula I, and the longest time for filtration was only 27 mins. In Comparative Example 1, 0.5 g of the compound of formula I was used to prepare the crystal of B82 type, which was of smaller scale, but the time needed for filtration was much longer than those of Examples 2-10. Therefore, the crystalline powder of the compound of formula I prepared in the present invention exhibits significant advantages in the process of filtration.

Example 12

In the present example, the drying processes of the samples obtained in Comparative Examples and Examples were compared.

5 g of solids were prepared according to the methods of Examples 2-10 and Comparative Examples 1-3 respectively, placed at 25° C., and vacuum-dried together with a water system until no organic solvent was detected through GC. The time for drying was compared, and the purity of the sample was analyzed. Specific results are shown in the following table:

| Sample | Bulk density (g/mL) | Purity before drying | Purity after drying | time Needed |
|---|---|---|---|---|
| Example 2 | 0.45 | 99.68% | 99.68% | 7 h |
| Example 3 | 0.43 | 99.63% | 99.61% | 6.5 h |
| Example 4 | 0.55 | 99.64% | 99.64% | 9 h |
| Example 5 | 0.6 | 99.52% | 99.47% | 10 h |
| Example 6 | 0.49 | 99.61% | 99.6% | 8.5 h |
| Example 7 | 0.6 | 99.65% | 99.57% | 9.5 h |
| Example 8 | 0.38 | 99.52% | 99.46% | 6 h |
| Example 9 | 0.54 | 99.42% | 99.38% | 8.5 h |
| Example 10 | 0.56 | 99.5% | 99.43% | 9 h |
| Comparative Example 1 | 0.85 | 99.26% | 97.96% | 25 h |
| Comparative Example 2 | / | 98.82% | 96.21% | 30 h |
| Comparative Example 3 | / | 98.74% | 96.17% | 32 h |

Example 13

Preparation of Pharmaceutical Composition

| Crystalline powder of the compound of formula I | Lactose | Anhydrous citric acid | Sodium hydroxide |
|---|---|---|---|
| 2.5 g | 20 g | q.s. | q.s. |

20 g of lactose were dissolved in purified water (200 ml) by heating at less than 50° C. After cooling to 20° C. or lower, 2.5 g of the crystalline powder of the compound of formula I obtained according to the method in Example 2 were added to the lactose solution, and gently agitated to avoid generation of bubbles. 2% aqueous citric acid solution (0.95 ml) were added, 0.4% aqueous sodium hydroxide solution (about 24 ml) were added to the solution to adjust pH to 5.5, and then diluted with pure water to give a volume of 250 ml. The resulting solution was dispensed into 100 vials of 10 ml volume, 2.5 ml per vial. The solution in each vial was lyophilized through a conventional method using a lyophilizer to obtain a lyophilized composition, each containing 25 mg of the crystalline powder of the compound of formula I.

Example 14

Preparation of Pharmaceutical Composition 0.2 g of the crystalline powder of the compound of formula I obtained according to the method in Example 2 were taken and prepared into an eye drop according to the method in Example 2 of US2007249546A1.

The embodiments described above are merely preferred embodiments of the present invention, and not provided to limit the scope of the substantial technical contents of the present invention, which are broadly defined in the claims of the present application. If any technical entity or method completed by other people is identical with that defined by the claims of the present application, or is an equivalent modification, all of them will be deemed as falling within the scope of the claims.

The invention claimed is:

1. A crystalline powder of a cyclic peptide compound of formula I, wherein a bulk density of the crystalline powder is less than 0.7 g/mL;

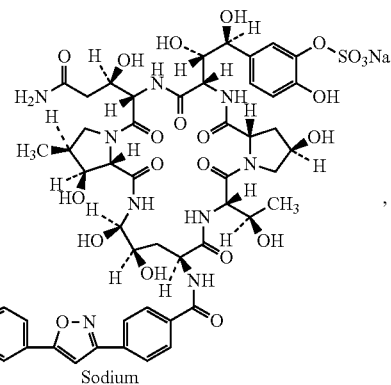

formula I and the crystalline powder has X-ray powder diffraction peaks at the following 2θ angles: 4.4±0.2°, 5.2±0.2°, 8.5±0.2°, and 9.6±0.2°.

2. The crystalline powder of the cyclic peptide compound according to claim 1, wherein the bulk density of the crystalline powder is less than 0.6 g/mL.

3. The crystalline powder of the cyclic peptide compound according to claim 1, wherein d50 of the crystalline powder is 10-100 um.

4. The crystalline powder of the cyclic peptide compound according to claim 1, wherein d10 of the crystalline powder is 1-9 um.

5. The crystalline powder of the cyclic peptide compound according to claim 1, wherein, before solid-liquid separation, d50 of the crystalline powder is 10-100 um.

6. The crystalline powder of the cyclic peptide compound according to claim 1, wherein, before solid-liquid separation, d10 of the crystalline powder is 1-9 um.

7. A preparation method for the crystalline powder of the cyclic peptide compound according to claim 1, comprising:
 (a) dissolving the cyclic compound of formula I in an aqueous mixed solution of alcohols to obtain a crystallization solution;
 (b) obtaining solids by reducing a temperature of the crystallization solution and/or adding an organic solvent (i) to the crystallization solution; and
 (c) vacuum-drying the solids obtained in step (b) in the presence of a water system, thereby obtaining the crystalline powder of the cyclic compound of formula I according to claim 1,
 in step (b), the organic solvent (i) includes at least one selected from the group consisting of n-propanol, isopropanol, isobutanol, methyl acetate, ethyl acetate, n-propyl acetate, and isopropyl acetate.

8. The preparation method of claim 7, wherein the aqueous mixed solution of alcohols in step (a) contains methanol and an alcohol that is selected from the group consisting of isobutanol, isopropanol, and n-propanol.

9. The preparation method of claim 8, wherein, in the aqueous mixed solution of alcohols in step (a), a volume ratio of methanol to the alcohol is 0.01-100.

10. The preparation method of claim 7, wherein, in the aqueous mixed solution of alcohols in step (a), a ratio of a total volume of the alcohols to a volume of water is 0.1 to 100.

11. The preparation method of claim 7, wherein, in step (b), the temperature is reduced to −40 to 35° C.

12. The preparation method of claim 7, wherein a volume ratio of the organic solvent (i) in step (b) to the aqueous mixed solution of alcohols in step (a) is 0.1 to 50.

13. The preparation method of claim 7, wherein the water system in step (c) is selected from the group consisting of tap water, pure water, ice-water mixture, and other substances capable of releasing water vapor.

14. A method for treating fungal infections comprising administrating the crystalline powder of the cyclic peptide compound according to claim 1 to a subject in need thereof.

15. A pharmaceutical composition comprising the crystalline powder of the cyclic peptide compound according to claim 1 and a pharmaceutically acceptable carrier.

16. A preparation method for a pharmaceutical composition, comprising:
mixing the crystalline powder of the cyclic peptide compound according to claim 1 and a pharmaceutically acceptable carrier.

17. The crystalline powder of the cyclic peptide compound according to claim 1, wherein a bulk density of the crystalline powder is less than 0.5 g/mL.

18. The crystalline powder of the cyclic peptide compound according to claim 1, wherein d50 of the crystalline powder is 20-50 um.

19. The crystalline powder of the cyclic peptide compound according to claim 1, wherein d10 of the crystalline powder is 1-5 um.

20. The crystalline powder of the cyclic peptide compound according to claim 1, wherein, before solid-liquid separation, d50 of the crystalline powder is 20-50 um.

21. The crystalline powder of the cyclic peptide compound according to claim 1, wherein, before solid-liquid separation, d10 of the crystalline powder is 3-6 um.

22. The preparation method of claim 8, wherein, in the aqueous mixed solution of alcohols in step (a), a volume ratio of methanol to the alcohol is 0.05-20.

23. The preparation method of claim 8, wherein, in the aqueous mixed solution of alcohols in step (a), a volume ratio of methanol to the alcohol is 0.1-10.

24. The preparation method of claim 7, wherein, in the aqueous mixed solution of alcohols in step (a), a ratio of a total volume of the alcohols to a volume of water is 0.5 to 10.

25. The preparation method of claim 7, wherein, in the aqueous mixed solution of alcohols in step (a), a ratio of a total volume of the alcohols to a volume of water is 1 to 7.

26. The preparation method of claim 7, wherein, in step (b), the temperature is reduced to −20 to 35° C.

27. The preparation method of claim 7, wherein, in step (b), the temperature is reduced to −10 to 30° C.

28. The preparation method of claim 7, wherein, in step (b), the temperature is reduced to −5 to 15° C.

29. The preparation method of claim 7, wherein a volume ratio of the organic solvent (i) in step (b) to the aqueous mixed solution of alcohols in step (a) is 0.1 to 10.

30. The preparation method of claim 7, wherein a volume ratio of the organic solvent (i) in step (b) to the aqueous mixed solution of alcohols in step (a) is 1-5.

* * * * *